United States Patent [19]

Komamiya et al.

[11] 4,288,403
[45] Sep. 8, 1981

[54] CHECKING PAPER FOR SHEET COMBUSTION TYPE OXYGEN CONCENTRATION MEASURING INSTRUMENT

[76] Inventors: Kogaku Komamiya, 438-7 Shimoishihara, Chofu, 182 Tokyo; Hajime Suzuki, 3-61 Shioiri-cho, Yokosuka-shi, Kanagawa-ken, both of Japan

[21] Appl. No.: 182,861

[22] Filed: Sep. 2, 1980

Related U.S. Application Data

[63] Continuation of Ser. No. 35,016, May 1, 1979, abandoned.

[51] Int. Cl.³ .................... G01N 7/00; G01N 31/12
[52] U.S. Cl. .................................. 422/83; 422/58; 23/232 R
[58] Field of Search .............. 23/232 R; 422/58, 78, 422/86–88, 94, 83; 73/19

[56] References Cited

U.S. PATENT DOCUMENTS 4,138,216  2/1979  Larsson et al. ............... 422/58 X

FOREIGN PATENT DOCUMENTS 50-2117 of 1975 Japan .

Primary Examiner—Michael S. Marcus
Attorney, Agent, or Firm—George B. Oujevolk

[57] ABSTRACT

A checking paper for use in a sheet combustion type oxygen concentration measuring instrument, comprising a thin sheet of paper bonded to plate-like holder made of cardboard, plastic or metal plate, said holder having a cutout portion of a suitable configuration such as an acute-angle isosceles triangle extending from one end of the holder to the other so that said paper sheet is partly exposed through said cutout portion of the holder. The base side end of the exposed portion of said paper sheet is extended beyond the open end of the holder and an igniting agent is provided to such extended portion, or the opening of the open end of said holder is widened to facilitate combustion and its propagation.

1 Claim, 10 Drawing Figures

FIG. 1 PRIOR ART
FIG. 2 PRIOR ART
FIG. 3
FIG. 4
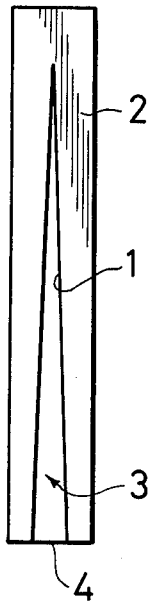
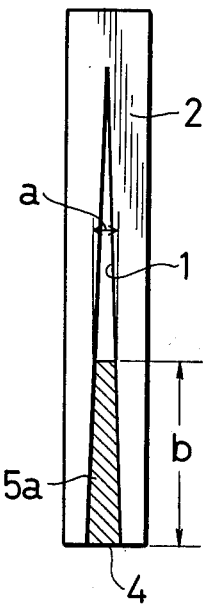
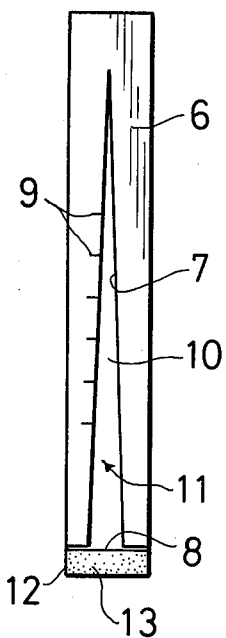
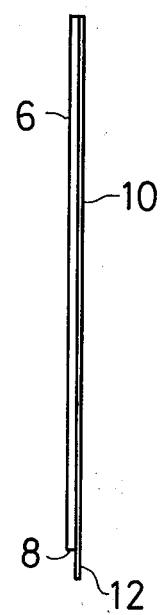
FIG. 5
FIG. 6
FIG. 7
FIG. 8
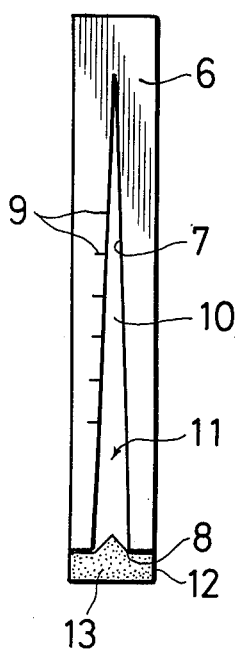
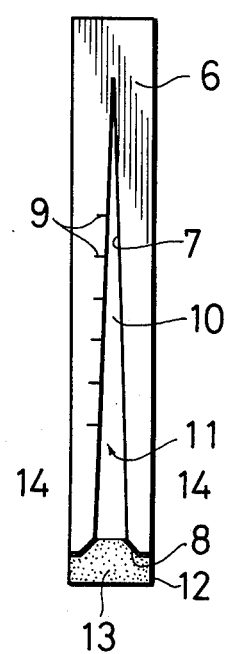
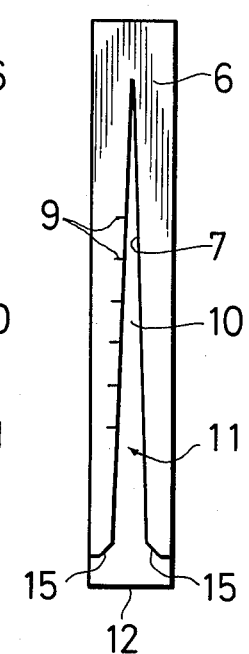
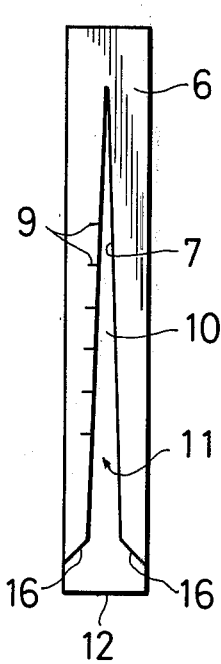

CHECKING PAPER FOR SHEET COMBUSTION TYPE OXYGEN CONCENTRATION MEASURING INSTRUMENT

This is a continuation of application Ser. No. 035,016, filed May 1, 1979, now abandoned.

BACKGROUND OF THE INVENTION

Oxygen is contained in air in a concentration of approximately 21%, and men breathe and treat fire in such atmosphere.

When the oxygen content in the air rises due to leak of oxygen from an oxygen source into a narrow space or for other reasons, there arise many abnormalities in such atmosphere, such as increased combustibility of clothes and lowered ignition point of the combustibles, resulting in the increased danger of a fire. On the other hand, in the atmosphere with too low oxygen content, man is asphyxiated.

Such excess or scarcity of oxygen can neither be scented nor visible, so that there are many occasions where man enters such locations unaware and gets burnt or suffocates to death.

So, when a person has need of entering a location where such danger is supposed to exist, he must analyze the oxygen content in the air to make sure of safety.

There are available various devices for such use, for example oxygen analyzer utilizing magnetism or oxygen cells or an indicator tube type oxygen sensor. However, these known devices are not necessarily satisfactory in respect of convenience in use at the site and other requirements such as long-time durability, simplicity and quick and safe analyzability.

BRIEF DESCRIPTION OF THE PRIOR ART

As an improved method for analyzing the atmosphere involving any danger of excess or scarcity of oxygen at the job site by a simple, quick and safe operation, there has been invented a so-called sheet combustion type oxygen concentration measuring method (Japanese Patent Publication No. 2117/75).

This method utilizes the following principle. As shown in FIG. 1 of the accompanying drawings, a thin sheet of paper 3 is pasted to a metallic holder 2 having a cutout 1 with the shape of an acute-angle equilateral triangle. When the paper sheet 3 is set alight from the open end (4) side of the holder 2, the fire spreads toward the inside of the cutout portion 1. Since the width of the paper sheet 3 narrows down as the combustion advances inwardly, the amount of heat produced by the combustion decreases gradually, but as heat value taken away by the metal portion is always the same regardless of the width of the paper sheet 3, combustion of sheet 3 cannot be sustained and finally the flame goes out.

Combustion of the paper sheet 3 is enhanced when the oxygen content is high but decreases as the oxygen content is lowered, so that the gap distance in the metallic holder at the position where the flame went out, that is, the gap distance shown by a in FIG. 2 is dependent on the oxygen content. In FIG. 2, b indicates the distance of combustion, 5a the burned-out portion of the paper sheet 3, and 5b the unburned portion of the paper sheet 3.

There is also available an instrument for measuring the oxygen concentration at the job site by using a checking paper of the same construction as shown in FIG. 1. According to this device, the checking paper is placed in a sealed container designed to allow feed and discharge of the sample gas and is supported therein so that the base of the exposed acute-angle isosceles triangle portion of the thin paper sheet is in contact with a nichrome wire, and said nichrome wire is electrified to set the paper sheet on fire.

This instrument, however, has some serious defects. Since the nichrome wire is expendable, it is adapted so that it is replacable together with the holder in which the nichrome wire is set, so that a positional aberration of the nichrome wire is liable to occur due to improper setting of the holder at the time of replacement. Also, there often takes place improper contact between the checking paper and the nichrome wire due to flexion of the nichrome wire in use or other causes.

If the paper is set on fire under such condition of improper contact, only a very limited part of the paper near the nichrome wire is burned and the flame goes out at an improper position. Thus, although the better part of the paper is left unburned, it can not be reused as the portion to be contacted with the nichrome wire is burned, and hence such paper is wasted. Also, when the paper is set on fire with the improper contact unnoticed, the operator might misjudge the oxygen content in the sample air by observing combustion of only a very limited portion of the paper.

OBJECT OF THE INVENTION

This invention has for its object to provide a checking paper to be used for measurement of oxygen concentration in the air in a limited area, wherein the checking paper is arranged to surely contact a nichrome wire set in the instrument to burn the paper so that combustion surely propagates along the exposed portion of the paper.

BRIEF DESCRIPTION OF THE DRAWINGS

FIG. 1 is a front view of a conventional checking paper;

FIG. 2 is a similar view to FIG. 1 but showing a mode of combustion of the paper;

FIG. 3 is a front view of a preferred embodiment of the checking paper in accordance with this invention;

FIG. 4 is a side view thereof;

FIG. 5 is a front view of a modification of the embodiment of FIG. 3;

FIG. 6 is a front view of another modification thereof;

FIG. 7 is a front view of another embodiment of the checking paper in accordance with this invention;

FIG. 8 is a front view of a modification of the embodiment of FIG. 7;

DETAILED DESCRIPTION OF THE INVENTION

Figure 9:
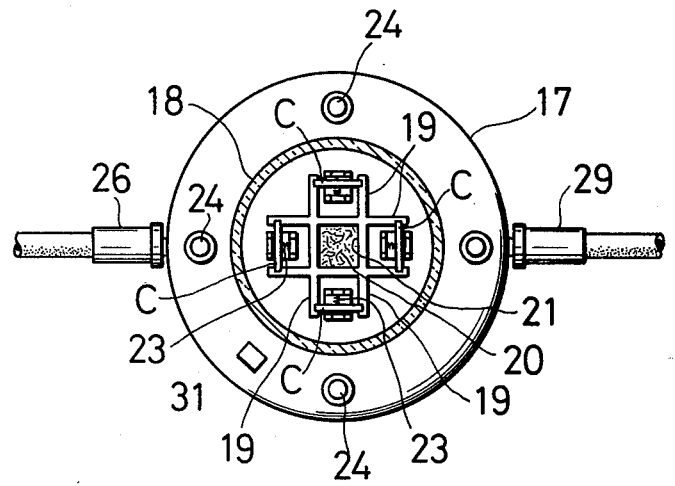
FIG. 9 is a plane view, with parts cut away, of an oxygen concentration measuring instrument using a checking paper according to this invention.

Now the invention is described in detail by way of its embodiments with reference to FIGS. 3 to 10 of the accompanying drawings.

Referring generally to the drawings, numeral 6 shows a holder made of an aluminum plate having a cutout portion 7 with the shape of an acute-angle isosceles triangle extending from one end of the plate to the other. The base of the triangle is open (8), and graduations 9 for indicating oxygen concentration in the air are provided along one of the two equal sides. Bonded to the entire backside surface of the holder 6 is a thin sheet of paper 10 which is exposed (11) through the triangle cutout portion 7 of the holder. The base side of the exposed portion 11 of said paper sheet 10 is extended out (12) beyond the open end 8 of the holder 6, and an igniting agent 13 is deposited on the entire surface of said extension 12 as shown in FIG. 3.

For the purpose of increasing the area of deposition, said igniting agent 13 may be provided not only on the extension 12 of the paper sheet 10 but also on a triangular portion which gets into the exposed area 11 of the paper sheet as shown in FIG. 5, or both corners of the open end 8 of the holder 6 may be cut out (14) and the igniting agent 13 may be provided on both the extention 12 of the paper sheet 10 and the portion extending into the exposed area 11 along a length corresponding to said cutouts 14 as shown in FIG. 6.

FIGS. 7 and 8 show the embodiments where no igniting agent is provided on the extension 12 of the paper sheet 10. In these embodiments, the opening of the open end 8 of the holder 6 is enlarged by cutting out the holder corners either rather limitedly (15, FIG. 7) or largely (16, FIG. 7) so as to facilitate propagation of paper combustion to the exposed area 11.

Figure 10:
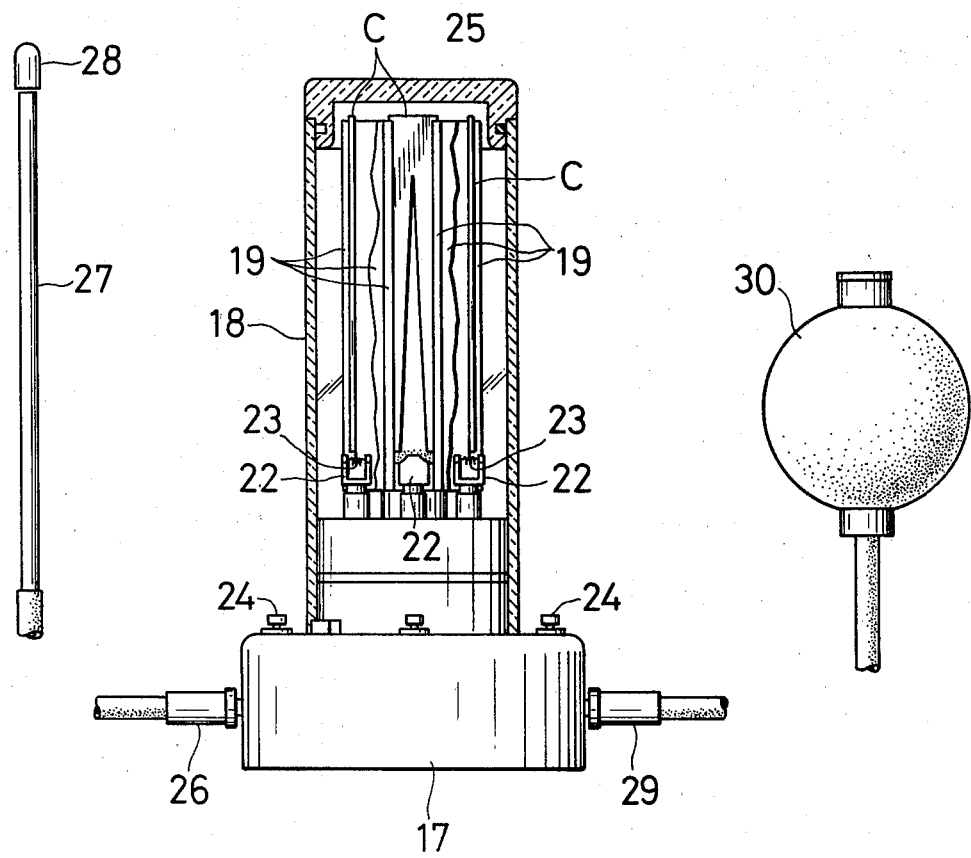
FIG. 10 is a side view thereof, with parts cut away.

Referring now to FIGS. 9 and 10, there is shown an example of instrument for measuring oxygen concentration by using a checking paper C such as described above. In these figures, numeral 17 indicates a stand and 18 shows a transparent sealed container mounted upright on said stand 17. Provided at the bottom of said container 18 are the guide rails 19 adapted for allowing vertical insertion of the checking paper C, said guide rails 19 being erected upright at four positions at 90° angular intervals in a way to define centrally thereof a desiccant compartment 21 where a desiccant 20 is packed. At the lower part of each of said guide rails 19 is provided a nichrome wire holder 22 adapted to support therein a nichrome wire 23 which is electrically charged by turning on the corresponding one of the ignition switches 24 provided along the circumference of the stand 17. The top of the container 18 is sealed airtightly by a cover 25. Provided in the stand 17 is a suction port 26 to which an air intake pipe 27 is connected. Numeral 28 designates a cap mounted at the end of the air intake pipe 27, 29 a discharge port provided in the stand 17 and connected to a rubber bulb 30, 31 a power switch, and 32 a packing.

In operation of this oxygen concentration measuring instrument, first the cover 25 is removed and then four sheets of checking paper C are inserted into the respective guide rails 19 whereby the extension 12 at the lower end of each paper sheet 10 is infallibly brought into contact with the corresponding nichrome wire 23 even if the paper sheet are slightly different from each other when inserted.

Then the cover 25 is placed in position to close the container 18 and the latter is carried to the site of measurement. The rubber bulb 30 is then operated by hand to purge air in the container 18 while the air of the site suctioned into the container 18 through the desiccant compartment 21. Thereafter, one of the ignition switches 24 is depressed, whereby the nichrome wire 23 corresponding to the depressed switch 24 is heated so that the extension 12 catches fire with the burning of the igniting agent 13 or by heating of the extension 12 itself, and the combustion propagated along the central portion of the exposed area 11 of the thin paper sheet 10.

The combustion keeps up until reaching a distance corresponding to the oxygen concentration in the air collected in the container 18 and, at this point, the flame goes out. Therefore, one can know the oxygen concentration in the air by reading the scale 9 on the holder 6.

For repeating the measurement at the same site or for performing measurements at different sites, the remaining three sheets of checking paper C are burned successively in the same way as hereinbefore described.

Although an aluminum plate is used as the checking paper holder in the foregoing embodiment, it is possible to use plates made of other metals, plastic, cardboard, etc. Also, the cutout in the holder may not necessarily be shaped as an acute-angle isosceles triangle but may be shaped into other suitable configurations. The checking paper may be bonded to a single holder plate as in the just described embodiment or may be sandwitched between two pieces of plate. It is also possible to provide only one nichrome wire 23 and only one ignition switch 24, with the respective sheets of checking paper C being arranged successively above the nichrome wire 23 so that they are turned in order and ignited upon every depression of the ignition switch. Checking paper may be burned by using other various kinds of heater means.

According to the device of this invention which has the foregoing construction, the e tension of flap at the end of each sheet of checking paper can be surely brought into contact with the heating element such as nichrome wire and the combustion can be infallibly propagated to the exposed area of the sheet, eliminating any possibility of mis-combustion which would be caused in use of the conventional checking paper. Thus, the device of this invention allows correct and sure measurement of oxygen concentration in the air and can avoid waste of checking paper. Also, if many sheets of checking paper are contained in the sealed container and arranged such that they are ignited in regular sequence, the measuring operation is markedly promoted in efficiency.

What is claimed is:

1. An instrument for measuring oxygen concentration by sheet combustion of a sheet of checking paper in a desired location, comprising in combination:

(a) a stand (17) with an outer portion, a suction port (26) with an intake pipe (27) connected thereto on one side thereof and a discharge port (29) on the other side thereof, a cap (28) for sealing said intake pipe suction port (26) when desired and a removable bulb (30) and a connecting pipe for mounting on said discharge port (29);

(b) a transparent tall sealed container (18) mounted on said stand (17);

(c) upright parallel guide rails (19) erected at a plurality of positions on said stand within said container (18) so disposed as to define centrally thereof a desiccant compartment (21) and a desiccant (20) packed therein;

(d) nichrome wire holder means (22) at the bottom of each of said guide rails for supporting a nichrome wire (23), and electrical switch means (24) on said stand outer portion for each of said holder means (22);

(e) paper holding means and checking paper bonded to said paper holding means, said paper holding means being a plate member sized and shaped for being held in said guide rails (19) and being provided with a cutout extending from one end of the plate member substantially to but not quite to the other end thereof and disposed so that said paper sheet has a partly exposed area (11) through said cutout in the holding means, said cutout having a general triangular shape with a wide portion towards the stand (17) and a narrow portion towards the top of said upright guide rails (19), said wide portion having an open end, said paper extending out beyond the open end of said holding means, said holding means having the corners of the open end so cut as to enlarge the opening thereat, said holding means and checking paper being so disposed in said rails (19) that the checking paper is brought into contact with the corresponding nichrome wire (23) so that the depression of said switch means (24) will heat up said nichrome wire and ignite said paper;

(f) a cover for said sealed container; and, (g) a scale along said cutout to indicate oxygen content.

* * * * *